US006464926B1

(12) United States Patent
Merrill et al.

(10) Patent No.: US 6,464,926 B1
(45) Date of Patent: Oct. 15, 2002

(54) PROCESS OF MAKING ULTRA HIGH MOLECULAR WEIGHT POLYETHYLENE PROSTHETIC DEVICES

(75) Inventors: Edward W. Merrill, Belmont, MA (US); William H. Harris, Belmont, MA (US); Premnath Venugopalan, Cambridge, MA (US); Murali Jasty, Weston, MA (US); Charles R. Bragdon, Weymouth, MA (US); Daniel O. O'Connor, East Taunton, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/542,476

(22) Filed: Apr. 4, 2000

Related U.S. Application Data

(60) Continuation of application No. 09/059,822, filed on Apr. 14, 1998, now abandoned, which is a division of application No. 08/600,744, filed on Feb. 13, 1996, now Pat. No. 5,879,400.

(51) Int. Cl.[7] ............................................. B29C 35/08
(52) U.S. Cl. ...................... 264/485; 264/162; 264/237; 264/488
(58) Field of Search ........................ 264/85, 162, 237, 264/485, 488

(56) References Cited

U.S. PATENT DOCUMENTS

| 3,297,641 A | 1/1967 | Werber et al. |
|---|---|---|
| 3,352,818 A | 11/1967 | Mever et al. |
| 3,758,273 A | 9/1973 | Johnston et al. |
| 3,944,536 A | 3/1976 | Lupton et al. |
| 4,586,995 A | 5/1986 | Randall et al. |
| 4,655,769 A | 4/1987 | Zachariades et al. |
| 4,747,990 A | 5/1988 | Gaussens et al. |
| 4,892,552 A | 1/1990 | Ainsworth et al. |
| 4,902,460 A | 2/1990 | Yagi et al. |
| 4,944,974 A | 7/1990 | Zachariades |
| 5,001,008 A | 3/1991 | Tokita et al. |
| 5,001,206 A | 3/1991 | Bashir et al. |
| 5,024,670 A | 6/1991 | Smith et al. |
| 5,037,928 A | 8/1991 | Li et al. |
| 5,059,196 A | 10/1991 | Coates |
| 5,066,755 A | 11/1991 | Lemstra |
| 5,160,464 A | 11/1992 | Ward et al. |
| 5,160,472 A | 11/1992 | Zachariades |

(List continued on next page.)

FOREIGN PATENT DOCUMENTS

| EP | 0373800 A1 | 6/1990 |
|---|---|---|
| EP | 0722973 A1 | 7/1996 |
| EP | 0729981 A1 | 9/1996 |
| EP | 0737481 A1 | 10/1996 |
| JP | 58157830 A | 9/1983 |
| JP | 04185651 A | 7/1992 |
| JP | 04198242 | 7/1992 |
| WO | WO98/01085 | 1/1998 |

OTHER PUBLICATIONS

Complaint (Dated Jun. 30, 1999).
Amended Complaint (Dated Jan. 6, 2000).

(List continued on next page.)

*Primary Examiner*—Leo B. Tentoni
(74) *Attorney, Agent, or Firm*—Heller Ehrman White & McAuliffe

(57) ABSTRACT

The present invention relates to a medical prosthesis for use within the body, which is formed of ultra high molecular weight polyethylene having a polymeric structure with less than about 50% crystallinity, less than about 290 Å lamellar thickness and less than about 940 MPa tensile elastic modulus, so as to reduce production of fine particles from the prosthesis during wear of the prosthesis. The present invention also relates to methods of manufacture of such devices and material used therein.

12 Claims, 3 Drawing Sheets

U.S. PATENT DOCUMENTS

| | | | |
|---|---|---|---|
| 5,407,623 | A | 4/1995 | Zachariades et al. |
| 5,414,049 | A | 5/1995 | Sun et al. |
| 5,449,745 | A | 9/1995 | Sun et al. |
| 5,466,530 | A | 11/1995 | England et al. |
| 5,478,906 | A | 12/1995 | Howard |
| 5,480,683 | A | 1/1996 | Chabrol et al. |
| 5,515,590 | A | 5/1996 | Pienkowski |
| 5,543,471 | A | 8/1996 | Sun et al. |
| 5,549,698 | A | 8/1996 | Averill et al. |
| 5,549,700 | A | 8/1996 | Graham et al. |
| 5,593,719 | A | 1/1997 | Dearnaley |
| 5,650,485 | A | 7/1997 | Sun et al. |
| 5,684,124 | A | 11/1997 | Howard et al. |
| 5,728,748 | A | 3/1998 | Sun et al. |
| 5,753,182 | A | 5/1998 | Higgins |
| 5,824,411 | A | 10/1998 | Shalaby et al. |
| 5,879,400 | A | 3/1999 | Merrill |
| 5,972,444 | A | 10/1999 | Patel et al. |
| 6,005,053 | A | 12/1999 | Parikh et al. |
| 6,017,975 | A | 1/2000 | Saum et al. |
| 6,168,626 | B1 | 1/2001 | Hyon et al. |
| 6,174,934 | B1 | 1/2001 | Sun et al. |
| 6,228,900 | B1 | 5/2001 | Shen et al. |
| 6,242,507 | B1 | 6/2001 | Saum et al. |
| 6,281,264 | B1 | 8/2001 | Salovey et al. |
| 6,316,158 | B1 | 11/2001 | Saum et al. |

OTHER PUBLICATIONS

Answer of Defendants Massachusetts Institute of Technology and The General Hospital Corporation to Amended Compliant and Amended Counter Claim (Date Jan. 7, 2000).

Reply of Plaintiff, Ambuj D. Sagar, Ph.D., to Amended Counterclaim of Defendants Massachusetts Institute of Technology and The General Hospital Corporation (Dated Jan. 18, 2000).

Atkinson Silane Cross–Linked HDPE for Prosthetic Applications, Polymers in Medicine and Surgery, Conf. Held by Plastics & Rubber Institute & Biol. Eng. Soc. (1989).

Dijkstra Et Al. Polymer 30: 866–873 (1989).

Gielenz Et Al. Colloid & Polymer Sci. 260:742–753 (1982).

Grobbelaar Et Al. J. of Bone and Joint Surgery 60–B(3): 370–374 (1978).

Jahan Et Al. J. of Biomed Material Research 25: 1005–1016 (1991).

Jones Et Al. Wear 70: 77–92 (1981).

Kang Et Al. J. of Amer. Chem. Society 89(9): 1980–1986 (1979).

Nusbaum Et Al. J. of Biomed Material Research 13: 557–576 (1979).

Oonishi Et Al. Super Low Wear Cross–Linked UHMWPE by Heavy High–Dose Gamma Radiation, WPOA $2^{ND}$ Congress of Hip Section, p.1 (1996).

Oonishi Et Al. Radia. Phys. Chem. 39(6): 495–504 (1992).

Oonishi Et Al. Encyclopedic Handbook of Biomaterials and Bioengineering, vol. 2, Marcel Dekker, Inc., 1853–1868 (1995).

Rose Et Al. J. of Orthopaedic Research Society 2(4): 393–400 (1984).

Saunders Et Al. Medical Device & Diagnostic Industry 222: 89–92 (1993).

Steicher Investigation on Sterilization and Modification of High Molecular Weight Polyethylenes by Ionizing Irradiation, Reprint from Betta–Gamma 1/89.

Am Soc. for Testing and Materials, Designation: E1649–94, 870–888 (1995).

PROCESS OF MAKING ULTRA HIGH MOLECULAR WEIGHT POLYETHYLENE PROSTHETIC DEVICES

This application is a continuation of U.S. Ser. No. 09/059,822 filed on Apr. 14, 1998, now abandoned, which is a divisional of 08/600,744 filed on Feb. 13, 1996, which issued as U.S. Pat. No. 5,879,400 on Mar. 9, 1999. The contents of these prior applications are hereby incorporated by reference.

FIELD OF THE INVENTION

The present invention relates to the orthopedic field and the provision of prostheses, such as hip and knee implants, as well as methods of manufacture of such devices and material used therein.

BACKGROUND OF THE INVENTION

The use of synthetic polymers, e.g., ultra high molecular weight polyethylene, with metallic alloys has revolutionized the field of prosthetic implants, e.g., their use in total joint replacements for the hip or knee. Wear of the synthetic polymer against the metal of the articulation, however, can result in severe adverse effects which predominantly manifest after several years. Various studies have concluded that such wear can lead to the liberation of ultrafine particles of polyethylene into the periprosthetic tissues. It has been suggested that the abrasion stretches the chain folded crystallites to form anisotropic fibrillar structures at the articulating surface. The stretched-out fibrils can then rupture, leading to production of submicron sized particles. In response to the progressive ingress of these polyethylene particles between the prosthesis and bone, macrophage-induced resorption of the periprosthetic bone is initiated. The macrophage, often being unable to digest these polyethylene particles, synthesize and release large numbers of cytokines and growth factors which can ultimately result in bone resorption by osteoclasts and monocytes. This osteolysis can contribute to mechanical loosening of the prosthesis components, thereby sometimes requiring revision surgery with its concomitant problems.

SUMMARY OF THE INVENTION

It is an object of the invention to provide an implantable prosthesis device formed at least in part of melt-irradiated ultra high molecular weight polyethylene (UHMWPE) which results in reduced production of fine particles from the prosthesis during wear of the prosthesis.

It is another object of the invention to reduce osteolysis and inflammatory reactions resulting from prosthesis implants.

It is yet another object of the invention to provide a prosthesis which can remain implanted within a person for prolonged periods of time.

It is yet another object of the invention to provide improved UHMWPE which can be used in the prostheses of the preceding objects.

Still another object of the invention is to provide improved UHMWPE which has a highly entangled and low crystalline polymeric structure.

A still further object of the invention is to provide improved UHMWPE which is relatively transparent and wear resistant.

According to the invention, a medical prosthesis for use within the body, e.g., for hip or knee joint replacement, is provided. It is formed at least in part of an UHMWPE which has a polymeric structure with less than about 50% crystallinity, less than about 290 Å lamellar thickness and less than about 940 MPa tensile elastic modulus, so as to reduce production of fine particles from the prosthesis during wear of the prosthesis. In one embodiment the UHMWPE has a polymeric structure with about 40% crystallinity, about 100 Å lamellar thickness and about 200 MPa tensile elastic modulus. Preferably, the UHMWPE has substantially no trapped free radicals, has reduced hardness, is substantially not oxidized, has substantially no chain scission, has extensive cross-linking so that a substantial portion of the zpolymeric structure does not dissolve in Decalin at 150° C. over a period of 24 hours, and/or has a high density of entanglement so as to cause the formation of imperfect crystals and reduce crystallinity. The UHMWPE initially has a molecular weight greater than about 500,000, preferably greater than about 1,000,000 and more preferably greater than about 2,000,000. In certain embodiments, part of the prosthesis is in the form of a cup shaped article having a load bearing surface made of this UHMWPE. This load bearing surface can be in contact with a second part of the prosthesis having a mating load bearing surface of a metallic or ceramic material.

Another aspect of the invention is UHMWPE having a unique polymeric structure characterized by less than about 50% crystallinity, less than about 290 Å lamellar thickness and less than about 940 MPa tensile elastic modulus. The UHMWPE can also have high transmissivity of light.

Yet other aspects of the invention are fabricated articles, e.g., with a load bearing surface, and transparent and wear resistant coatings, made from such UHMWPE. One embodiment is where the fabricated article is in the form of a bar stock which is capable of being shaped into articles by conventional methods, e.g., machining.

Yet another aspect of the invention includes a method for making highly entangled and crosslinked UHMWPE. Conventional UHMWPE, in the form of, e.g., a powder, a bar stock, a shaped bar stock, a coating or a fabricated article, e.g., a cup shaped article for use in a prosthesis, is provided. Preferably, the UHMWPE starting material has an average molecular weight of greater than about 2 million. The UHMWPE is surrounded with an inert material that is substantially free of oxygen. The UHMWPE is heated at or above its melting temperature, preferably, at about 145° C. to about 230° C., more preferably at about 175° C. to about 200° C., for a time sufficient to allow the polymer chains to achieve an entangled state, e.g., for a period of about 5 minutes to about 3 hours. The heated UHMWPE is then crosslinked so as to trap the polymer chains in the entangled state using irradiation, e.g., with gamma irradiation or electron irradiation, preferably allowing a dose greater than about 1 MRad, more preferably a dose greater than about 20 MRad. The irradiated UHMWPE is then cooled to about 250° C., preferably at a rate equal to or greater than about 0.5° C./min., more preferably at a rate equal to or greater than about 120° C./min. In certain embodiments, the cooled UHMWPE is then machined or compression molded.

Yet another aspect of the invention includes the product made in accordance with this method.

The invention also features a method of making a prosthesis from UHMWPE so as to reduce production of fine particles from the prosthesis during wear of the prosthesis. UHMWPE having a polymeric structure with less than about 50% crystallinity, less than about 290 Å lamellar thickness and less than about 940 MPa tensile elastic modulus is provided. A prosthesis is formed from this UHMWPE, the UHMWPE forming a load bearing surface of the prosthesis.

Yet another aspect of the invention includes a method of treating a body in need of a prosthesis. A shaped prosthesis formed of ultra high molecular weight polyethylene having a polymeric structure with less than about 50% crystallinity, less than about 290 Å lamellar thickness and less than about 940 MPa tensile elastic modulus, is provided. This prosthesis is applied to the body in need of the prosthesis.

The above and other objects, features and advantages of the present invention will be better understood from the following specification when read in conjunction with the accompanying drawings.

DETAILED DESCRIPTION

This invention provides a medical prosthesis for use within the body which is formed of ultra high molecular weight polyethylene (UHMWPE) which has a polymeric structure with less than about 50% crystallinity, less than about 290 Å lamellar thickness and less than about 940 MPa tensile elastic modulus, so as to reduce production of fine particles from the prosthesis during wear of the prosthesis.

Figure 1:
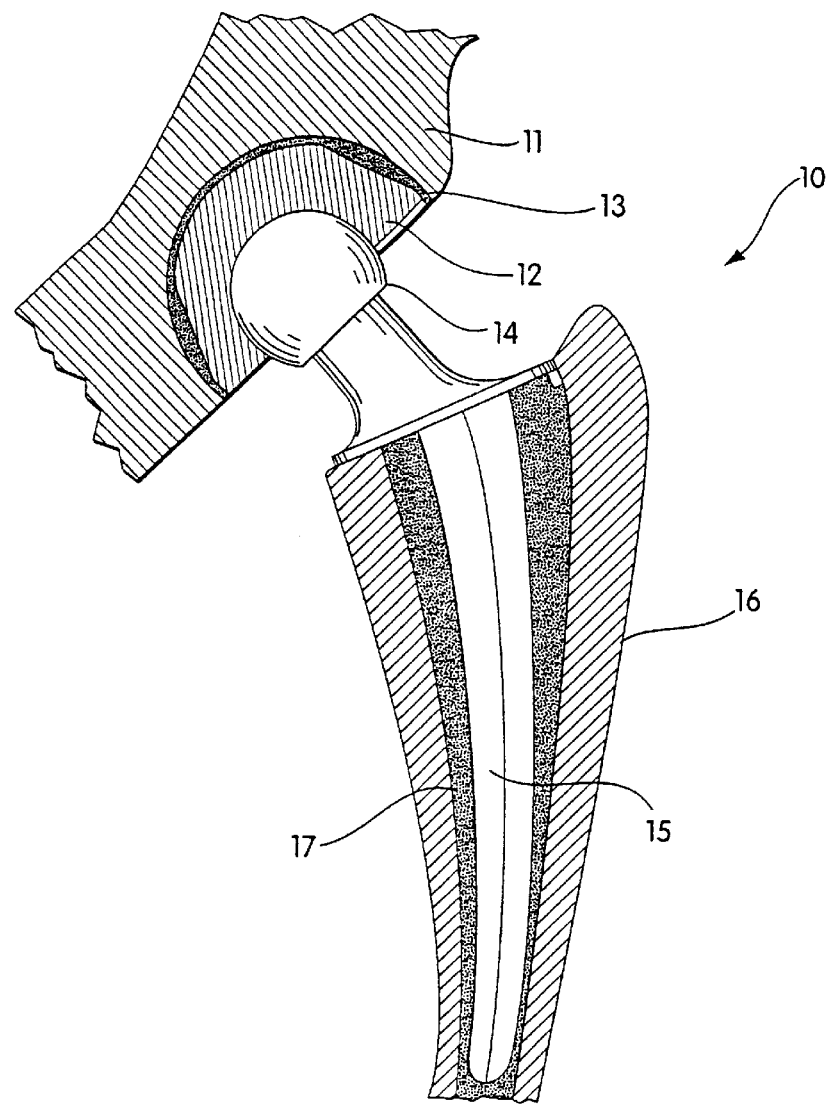
FIG. 1 is a cross-sectional view through the center of a medical hip joint prosthesis in accordance with a preferred embodiment of this invention.

A medical prosthesis in the form of a hip joint prosthesis is generally illustrated at 10 in FIG. 1. The prosthesis shown has a conventional ball head 14 connected by a neck portion to a stem 15 which is mounted by conventional cement 17 to the femur 16. The ball head can be of conventional design and formed of stainless steel or other alloys as known in the art. The radius of the ball head closely conforms to the inner cup radius of an acetabular cup liner 12 which can be mounted in cement 13 directly to the pelvis 11. Alternatively, a metallic acetabular cup can be cemented to the pelvis and the cup liner 12 can form a coating or liner connected to the cup by cement or other means as known in the art.

The specific form of the prosthesis can vary greatly as known in the art. Many hip joint constructions are known and other prostheses such as knee joints are known. All such prior art prostheses can be benefited by making at least one load bearing surface of such prosthesis of a high molecular weight polyethylene material in accordance with this invention. Such load bearing surfaces can be in the form of layers, linings or actual whole devices as shown in FIG. 1. In all cases, it is preferred that the load bearing surface act in conjunction with a metallic or ceramic mating member of the prosthesis so that a sliding surface is formed therebetween. Such sliding surfaces are subject to breakdown of the polyethylene as known in the prior art. Such breakdown can be greatly diminished by use of the materials of the present invention.

Figure 2:
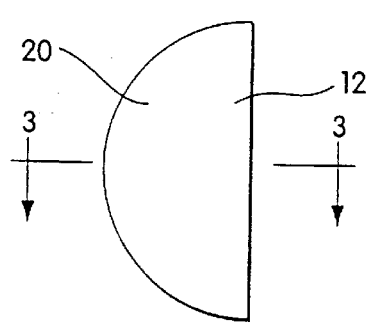
FIG. 2 is a side view of an acetabular cup liner as shown in FIG. 1.
Figure 3:
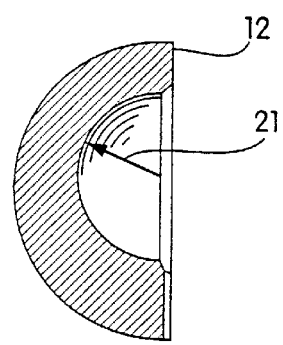
FIG. 3 is a cross-sectional view through line 3—3 of FIG. 2.

FIG. 2 shows the cup liner in the form of a half hollow ball-shaped device better seen in the cross-section of FIG. 3. As previously described, the outer surface 20 of the cup liner need not be circular or hemispherical but can be square or of any configuration to be adhered directly to the pelvis or to the pelvis through a metallic cup as known in the art. The radius of the cup liner shown at 21 in FIG. 3 of the preferred embodiment ranges from about 20 mm to about 35 mm. The thickness of the cup liner from its generally hemispherical hollow portion to the router surface 20 is preferably about 8 mm. The outer radius is preferably in the order of about 20 mm to about 35 mm.

In some cases, the ball joint can be made of the UHMWPE of this invention and the cup formed of metal, although it is preferred to make the cup or cup liner of UHMWPE to mate with the metallic ball. The particular method of attachment of the components of the prosthesis to the bones of the body can vary greatly as known in the art.

The medical prosthesis includes, e.g., orthopedic joint and bone replacement parts, e.g., hip, knee, elbow or ankle replacements. The prosthesis can be in the form of a cup shaped article which has a load bearing surface. Medical prostheses are also meant to include any wearing surface of a prosthesis, e.g., a coating on a surface of a prosthesis in which the prosthesis is made from a material other than the UHMWPE of this invention.

The prostheses of this invention are useful for contact with metal containing parts formed of, e.g., stainless steel, titanium alloy or nickel cobalt alloy, or with ceramic containing parts. For example, a hip joint is constructed in which a cup shaped article having an inner radius of 25 mm, is contacted with a metal ball having an outer radius of 25 mm, so as to closely mate with the cup shaped article. The load bearing surface of the cup shaped article of this example is made from the UHMWPE of this invention, preferably having a thickness of at least about ¼ inch and more preferably having a thickness of about ⅓ inch or more.

The prostheses can have any standard known form, shape, or configuration, or be a custom design, but have at least one load bearing surface of UHMWPE of this invention.

The prostheses of this invention are non-toxic to humans. They are not subject to deterioration by normal body constituents, e.g., blood or interstitial fluids. They are capable of being sterilized by standard means, including, e.g., heat or irradiation.

By UHMWPE is meant linear non-branched chains of ethylene that have molecular weights in excess of about 500,000, preferably above about 1,000,000, and more preferably above about 2,000,000. Often the molecular weights can reach about 8,000,000. By initial average molecular weight is meant the average molecular weight of the UHMWPE starting material, prior to any irradiation.

The UHMWPE of this invention has a polymeric structure with less than about 50% crystallinity, preferably less than about 40% crystallinity, more preferably less than about 35% crystallinity, and most preferably less than about 30% crystallinity. By crystallinity is meant the fraction of the polymer that is crystalline. The crystallinity is calculated by knowing the weight of the sample (w, in g), the heat absorbed by the sample in melting (E, in cal) and the heat of melting of polyethylene crystals (ΔH=69.2 cal/g), and using the following equation:

$$\% \ crystallinity = \frac{E}{w \cdot \Delta H}$$

The UHMWPE of this invention has a polymeric structure with less than about 290 Å lamellar thickness, preferably less than about 200 Å lamellar thickness, and most preferably less than about 100 Å lamellar thickness. By lamellar thickness (l) is meant the calculated thickness of assumed lamellar structures in the polymer using the following expression:

$$l = \frac{2 \cdot \sigma_e \cdot T^\circ_m}{\Delta H \cdot (T^\circ_m - T_m) \cdot \rho}$$

where, $\sigma_e$ is the end free surface energy of polyethylene (2.22×10$^{-6}$ cal/cm$^2$), ΔH is the heat of melting of polyethylene crystals (69.2 cal/g), $\rho$ is the density of the crystalline regions (1.005 g/cm$^3$), $T_m^\circ$ is the melting point of a perfect polyethylene crystal (418.15K) and $T_m$ is the experimentally determined melting point of the sample.

The UHMWPE of this invention has less than about 940 MPa tensile elastic modulus, preferably less than about 600 MPa tensile elastic modulus, more preferably less than about 400 MPa tensile elastic modulus, and most preferably less than about 200 MPa tensile elastic modulus. By tensile elastic modulus is meant the ratio of the nominal stress to corresponding strain for strains less than 0.5% as determined using the standard test ASTM 638 M III.

In one embodiment, the UHMWPE of this invention has a polymeric structure with about 40% crystallinity, about 100 Å lamellar thickness and about 200 MPa tensile elastic modulus.

It is preferred that the UHMWPE have no trapped free radicals, especially unsaturated trans-vinylene free radicals. It is preferred that the UHMWPE have a hardness less than about on the Shore D scale, more preferably a hardness less than about 55 on the Shore D scale, most preferably a hardness less than about 50 on the Shore D scale. By hardness is meant the instantaneous indentation hardness measured on the Shore D scale using a durometer described in ASTM D2240. It is preferred that the UHMWPE be substantially not oxidized and/or have substantially no chain scission. By substantially not oxidized is meant that the ratio of the area under the carbonyl peak at 1740 cm$^{-1}$ in the FTIR spectra to the area under the peak at 1460 cm$^{-1}$ in the FTIR spectra of the melt-irradiated sample be of the same order of magnitude as the ratio for the sample before melt irradiation. By substantially no chain scission is meant that the fraction of the polymer sample dissolving in normal xylene at 130° C. and remaining in solution after cooling to room temperature be less than or equal to the fraction of the conventional UHMWPE dissolving in normal xylene at 130° C. and remaining in solution after cooling to room temperature within the margins of experimental error. In some embodiments, the polymeric structure has extensive crosslinking such that a substantial portion of the polymeric structure does not dissolve in Decalin. By substantial portion is meant at least 50% of the polymer sample's dry weight. By not dissolve in Decalin is meant does not dissolve in Decalin at 150° C. over a period of 24 hours. Preferably, the UHMWPE has a high density of entanglement so as to cause the formation of imperfect crystals and reduce crystallinity.

By the density of entanglement is meant the number of points of entanglement of polymer chains in a unit volume; a higher density of entanglement being indicated by the polymer sample's inability to crystallize to the same extent as conventional UHMWPE, thus leading to a lesser degree of crystallinity.

The polymeric structure of the UHMWPE used in the prostheses of this invention results in the reduction of production of fine particles from the prosthesis during wear of the prosthesis. As a result of the limited number of fine polyethylene particles being shed into the body, the prosthesis exhibits longer implant life. Preferably, the prosthesis can remain implanted in the body for at least 10 years, more preferably for at least 20 years and most preferably for the entire lifetime of the patient.

The invention also includes other fabricated articles made from UHMWPE having a polymeric structure with less than about 50% crystallinity, less than about 290 Å lamellar thickness and less than about 940 MPa tensile elastic modulus. Such articles include shaped articles and unshaped articles, including, e.g., machined or molded objects, e.g., cups, gears, nuts, sled runners, bolts, fasteners and the like, and bar stock, films, cylindrical bars, sheeting, panels, and fibers. Shaped articles can be made, e.g., by machining. The fabricated articles are particularly suitable for load bearing applications, e.g., as a load bearing surface, and as metal replacement articles. Thin films or sheets of UHMWPE, which have been melt-irradiated can also be attached, e.g., with glue, onto supporting surfaces, and thus used as a transparent, wear resistant load bearing surface.

The invention also includes UHMWPE which has a unique polymeric structure characterized by less than about 50% crystallinity, less than about 290 Å lamellar thickness and less than about 940 MPa tensile elastic modulus. Depending upon the particular processing used to make the UHMWPE, certain impurities may be present in the UHMWPE of this invention, including, e.g., calcium stearate, mold release agents, extenders, anti-oxidants and/or other conventional additives to polyethylene polymers. In certain embodiments, the UHMWPE has high transmissivity of light, preferably a transmission greater than about 10% of light at 517 nm through a 1 mm thick sample, more preferably a transmission greater than about 30% of light at 517 nm through a 1 mm thick sample, and most preferably a transmission greater than about 40% of light at 517 nm through a 1 mm thick sample. Such UHMWPE is particularly useful for thin films or sheets which can be attached onto supporting surfaces of various articles, the film or sheet being transparent and wear resistant.

This invention also provides a method for making UHMWPE which is highly entangled and crosslinked. Preferably, this UHMWPE has a polymeric structure with less than about 50% crystallinity, less than about 290 Å lamellar thickness and less than about 940 MPa tensile elastic modulus. Conventional UHMWPE, e.g., a powder, a bar stock, a shaped bar stock, a coating, or a fabricated article is provided. By conventional UHMWPE is meant commercially available high density (linear) polyethylene of molecular weights greater than about 500,000. Preferably, the UHMWPE starting material has an average molecular weight of greater than about 2 million. By initial average molecular weight is meant the average molecular weight of the UHMWPE starting material, prior to any irradiation. This UHMWPE is surrounded with an inert material that is substantially free of oxygen, e.g., nitrogen, argon or helium. The UHMWPE is heated above its melting temperature for a time sufficient to allow the UHMWPE chains to take up an entangled state. Preferably, the temperature is about 145° C. to about 230° C., and more preferably, is about 1750 to about 200° C. The period of time of heating should be sufficient to permit the UHMWPE polymer chains to take up a random coil conformation. Preferably, the heating is maintained so to keep the polymer at the preferred temperature for about 5 minutes to about 3 hours, and more preferably for about 30 minutes to about 2 hours. The UHMWPE is then irradiated so as to trap the polymer chains in the entangled state, e.g., with gamma irradiation or electron irradiation. In general, gamma irradiation gives a high penetration depth but takes a longer time, resulting in increased cost of operation and the possibility of some oxidation. In general, electron irradiation gives more limited penetration depths but takes a shorter time, and hence the cost and the possibility of oxidation is reduced. The irradiation dose can be varied to control the degree of crosslinking and crystallinity in the final UHMWPE product. Preferably, a dose of greater than about 1 MRad is used, more preferably a dose of greater than about 20 MRad is used. When electron irradiation is used, the energy of the electrons can be varied to change the depth of penetration of the electrons, thereby controlling the degree of crosslinking and crystallinity in the final UHMWPE product. Preferably, the energy is about 0.5 MeV to about 10 MeV, more preferably about 1 MeV to about 5 MeV. Such manipulability is particularly useful when the irradiated object is an article of varying thickness or depth, e.g., an articular cup for a prosthesis. The irradiated UHMWPE is then cooled to about 25° C. so as to produce UHMWPE with lower crystallinity than the starting material. Faster cooling rates are preferred. Preferably, the cooling rate is equal to or greater than about 0.5° C./min, more preferably equal to or greater than about 120° C./min. In certain embodiments, the cooled UHMWPE can be machined. Examples 1, 3 and 6 describe preferred embodiments of the method. Examples 2, 4 and 5, and FIGS. 4 through 7, illustrate certain properties of the melt-irradiated UHMWPE obtained from these preferred embodiments, as compared to conventional UHMWPE.

Conventional UHMWPE is standardly generated by Ziegler-Natta catalysis, and as the polymer chains are generated from the surface catalytic site, they crystallize, and interlock as crystal folded chains. Examples of known UHMWPE include Hifax Grade 1900 polyethylene (obtained from Himont USA Corp., Wilmington, Delaware) and Hoechst-Celanese GUR-415 polyethylene (obtained from Hoechst-Celanese Corp., Houston, Tex.). Without being bound by any theory, it is believed that if this UHMWPE is subjected to temperatures above the melting point ($T_m$ approximately 135° C.), and if given enough time to relax, each UHMWPE chain should adopt the unperturbed random walk conformation which should lead to enormous chain entanglement. Irradiating the melted UHMWPE should trap the polymers in this entangled state. Upon cooling below the melting point, these entangled chains should be limited in their ability to crystallize by chain folding. The crystallinity should be limited to very small clusters which are connected by amorphous sections, and which have minimum chain folding. Such a form of UHMWPE should therefore better resist the shedding of fine polyethylene particles which currently processed conventional UHMWPE experiences under conditions of wear, e.g., under sliding friction in a joint.

This invention also includes the product made in accordance with the above described method.

Also provided in this invention is a method of making a prosthesis from UHMWPE so as to reduce production of fine particles from the prosthesis during wear of the prosthesis. UHMWPE having a polymeric structure with less than about 50% crystallinity, less than about 290 Å lamellar thickness and less than about 940 MPa tensile elastic modulus is provided. A prosthesis is formed from this UHMWPE, the UHMWPE forming a load bearing surface of the prosthesis. Formation of the prosthesis can be accomplished by standard procedures known to those skilled in the art, e.g., machining.

Also provided in this invention is a method of treating a body in need of a prosthesis. A shaped prosthesis formed of ultra high molecular weight polyethylene having a polymeric structure with less than about 50% crystallinity, less than about 290 Å lamellar thickness and less than about 940 MPa tensile elastic modulus, is provided. This prosthesis is applied to the body in need of the prosthesis. The prosthesis reduces production of fine particles from the prosthesis during wear of the prosthesis. In preferred embodiments, the ultra high molecular weight polyethylene forms a load bearing surface of the prosthesis.

The products and processes of this invention also apply to other polymeric materials such as high-density-polyethylene, low-density-polyethylene, linear-low-density-polyethylene and polypropylene.

EXAMPLES

Example 1

Method of Making Melt-Irradiated UHMWPE

This example illustrates electron irradiation of melted UHMWPE.

A cuboidal specimen of size 10 mm×12 mm×60 mm, prepared from conventional ram extruded UHMWPE bar stock (GUR 415, obtained from Westlake Plastics, Lenni, Pa.) was placed in a chamber. The atmosphere within the chamber consisted of low oxygen nitrogen gas (<0.5 ppm oxygen gas) (obtained from AIRCO, Murray Hill, N.J.). The pressure in the chamber was approximately 1 atm. The temperature of the sample and the irradiation chamber was controlled using a heater, a variac and a thermocouple readout (manual) or temperature controller (automatic). The chamber was heated with a 270 W heating mantle. The chamber was heated (controlled by the variac) at a rate such that the steady state temperature of the sample was about 175° C. The sample was held at the steady state temperature for 30 minutes before starting the irradiation.

Irradiation was done using a van de Graaff generator with electrons of energy 2.5 MeV and a dose rate of 1.67 MRad/min. The sample was given a dose of 20 MRad with the electron beam hitting the sample on the 60 mm×12 mm surface. The heater was switched off after irradiation, and the sample was allowed to cool within the chamber under inert atmosphere, nitrogen gas, to 25° C. at approximately 0.5° C./minute. As a control, similar specimens were prepared using unheated and unirradiated bar stock of conventional UHMWPE.

Example 2

Comparison of Properties of GUR 415 UHMWPE Bar Stock and Melt-Irradiated GUR 415 UHMWPE Bar Stock (20 MRad)

This example illustrates various properties of the irradiated and unirradiated samples of UHMWPE bar stock (GUR 415) obtained from Example 1. The tested samples were as follows: the test sample was bar stock which was molten and then irradiated while molten; control was bar stock (no heating/melting, no irradiation).

(A) Differential Scanning Calorimetry (DSC)

A Perkin-Elmer DSC7 was used with an ice-water heat sink and a heating and cooling rate of 10° C./minute with a continuous nitrogen purge. The crystallinity of the samples obtained from Example 1 was calculated from the weight of the sample and the heat of melting of polyethylene crystals (69.2 cal/g). The temperature corresponding to the peak of the endotherm was taken as the melting point. The lamellar thickness was calculated by assuming a lamellar crystalline morphology, and knowing the heat of crystallization (69.2 cal/g), the melting point of a perfect crystal (418.15 K), the density of the crystalline regions (1.005 g/cm$^3$) and the end free surface energy of polyethylene ($2.22 \times 10^{-6}$ cal/cm$^2$). The results are shown in Table 1 and FIG. 4.

TABLE 1

DSC (10° C./min)

| Property | GUR 415 (unirradiated) 0 MRad | GUR 415 (melt-irradiated) 20 MRad |
|---|---|---|
| Crystallinity (%) | 50.2 | 37.8 |
| Melting Point (C.) | 135.8 | 125.5 |
| Lamellar thickness (A) | 290 | 137 |

The results indicate that the melt-irradiated sample had a more entangled and less crystalline polymeric structure than the unirradiated sample, as evidenced by lower crystallinity, lower lamellar thickness and lower melting point.

(B) Swell Ratio

The samples were cut into cubes of size 2 mm×2 mm×2 mm and kept submerged in Decalin at 150° C. for a period of 24 hours. An antioxidant (1% N-phenyl-2-naphthylamine) was added to the Decalin to prevent degradation of the sample. The swell ratio and percent extract were calculated by measuring the weight of the sample before the experiment, after swelling for 24 hours and after vacuum drying the swollen sample. The results are shown in Table 2.

TABLE 2

Swelling in Decalin with Antioxidant for 24 hours at 150° C.

| Property | GUR 415 (unirradiated) 0 MRad | GUR 415 (melt-irradiated) 20 MRad |
|---|---|---|
| Swell Ratio | dissolves | 2.5 |
| Extract (%) | approx. 100% | 0.0 |

The results indicate that the melt-irradiated UHMWPE sample was highly crosslinked, and hence did not allow dissolution of polymer chains into the hot solvent even after 24 hours, while the unirradiated sample dissolved completely in the hot solvent in the same period.

(C) Tensile Elastic Modulus

ASTM 638 M III of the samples was followed. The strain was 1 mm/minute. The experiment was performed on a MTS machine. The results are shown in Table 3.

TABLE 3

Elastic Test (ASTM 638 M III, 1 mm/min.

| Property | GUR 415 (unirradiated) 0 MRad | GUR 415 (melt-irradiated) 20 MRad |
|---|---|---|
| Tensile Elastic modulus (MPa) | 940.7 | 200.8 |
| Yield stress (MPa) | 22.7 | 14.4 |
| Strain at break (%) | 953.8 | 547.2 |
| Engineerinq UTS (MPa) | 46.4 | 15.4 |

The results indicate that the melt-irradiated UHMWPE sample had a significantly lower tensile elastic modulus than the unirradiated control. The lower strain at break of the melt-irradiated UHMWPE sample is yet further evidence for the crosslinking of chains in that sample.

(D) Hardness

The hardness of the samples was measured using a durometer on the shore D scale. The hardness was recorded for instantaneous indentation. The results are shown in Table 4.

TABLE 4

Hardness (Shore D)

| Property | GUR 415 (unirradiated) 0 MRad | GUR 415 (melt-irradiated) 20 MRad |
|---|---|---|
| Hardness (D Scale) | 65.5 | 54.5 |

The results indicate that the melt-irradiated UHMWPE was softer than the unirradiated control.

(E) Light Transmissivity (transparency)

Transparency of the samples was measured as follows: Light transmission was studied for a light of wave length 517 nm passing through a sample of approximately 1 mm in thickness placed between two glass slides. The samples were prepared by polishing the surfaces against 600 grit paper. Silicone oil was spread on the surfaces of the sample and then the sample was placed in between two slides. The silicone oil was used in order to reduce diffuse light scattering due to the surface roughness of the polymer sample. The reference used for this purpose was two similar glass slides separated by a thin film of silicone oil. The transmissivity was measured using a Perkin Elmer Lambda 3B uv-vis spectrophotometer. The absorption coefficient and transmissivity of a sample exactly 1 mm thick were calculated using the Lambert-Beer law. The results are shown in Table 5.

TABLE 5

Transmissivity of Light at 517 nm

| Property | GUR 415 (unirradiated) 0 MRad | GUR 415 (melt-irradiated) 20 MRad |
|---|---|---|
| Transmission (%) (1 mm sample) | 8.59 | 39.9 |
| Absorption coefficient (cm$^1$) | 24.54 | 9.18 |

The results indicate that the melt-irradiated UHMWPE sample transmitted much more light through it than the control, and hence is much more transparent than the control.

(F) Environmental Scanning Electron Microscopy (ESEM)

ESEM (ElectroScan, Model 3) was performed on the samples at 10 kV (low voltage to reduce radiation damage to the sample) with an extremely thin gold coating (approximately 20 Å to enhance picture quality). By studying the surface of the polymer under the ESEM with and without the gold coating, it was verified that the thin gold coating did not produce any artifacts.

The samples were etched using a permanganate etch with a 1:1 sulfuric acid to orthophosphoric acid ratio and a 0.7% (w/v) concentration of potassium permanganate before being viewed under the ESEM.

Figure 4:
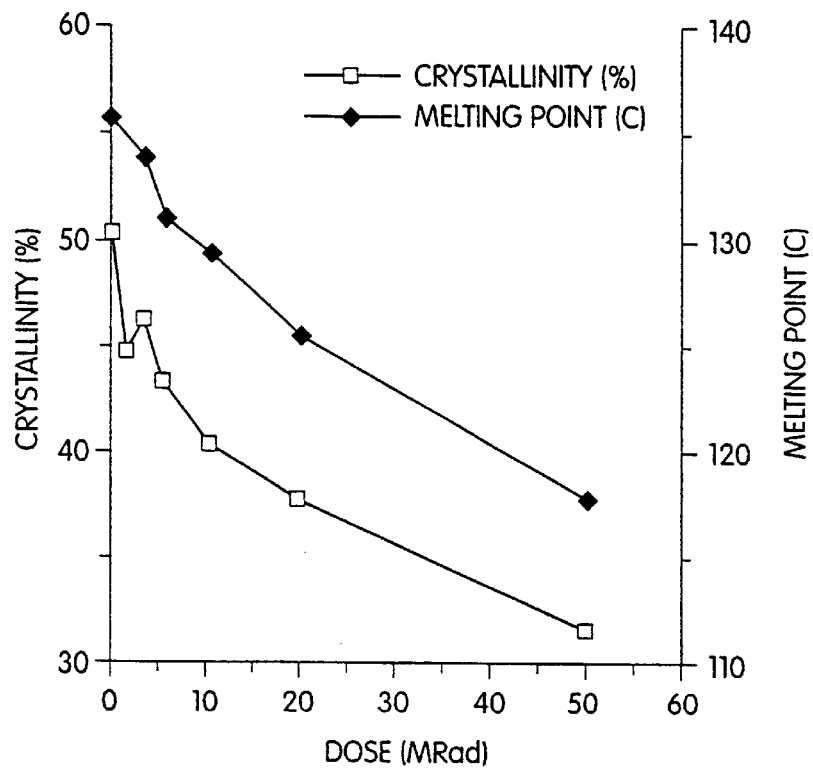
FIG. 4 is a graph showing the crystallinity and melting point of melt-irradiated UHMWPE at different irradiation doses.
Figure 5:
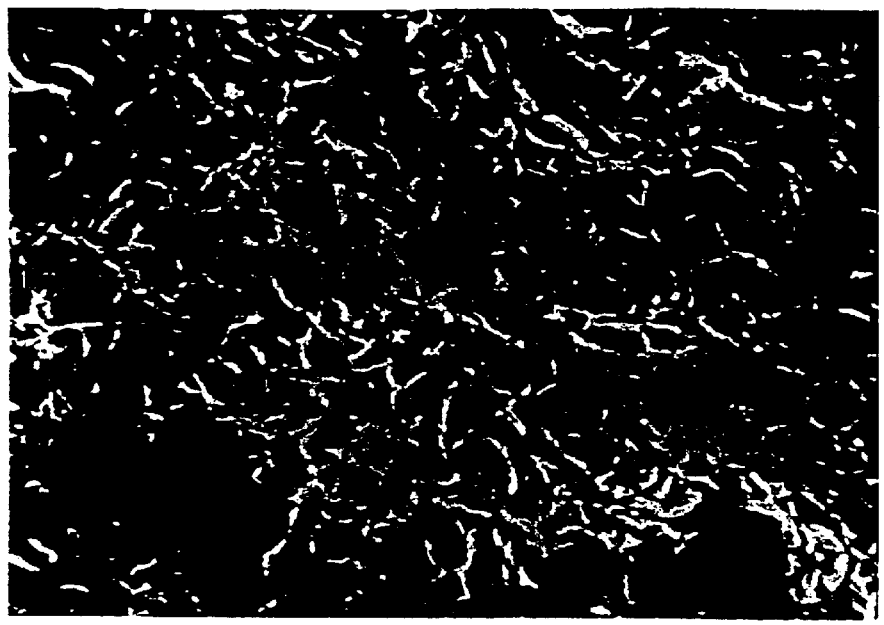
FIG. 5 is an environmental scanning electron micrograph of an etched surface of conventional UHMWPE showing its crystalline structure.
Figure 6:
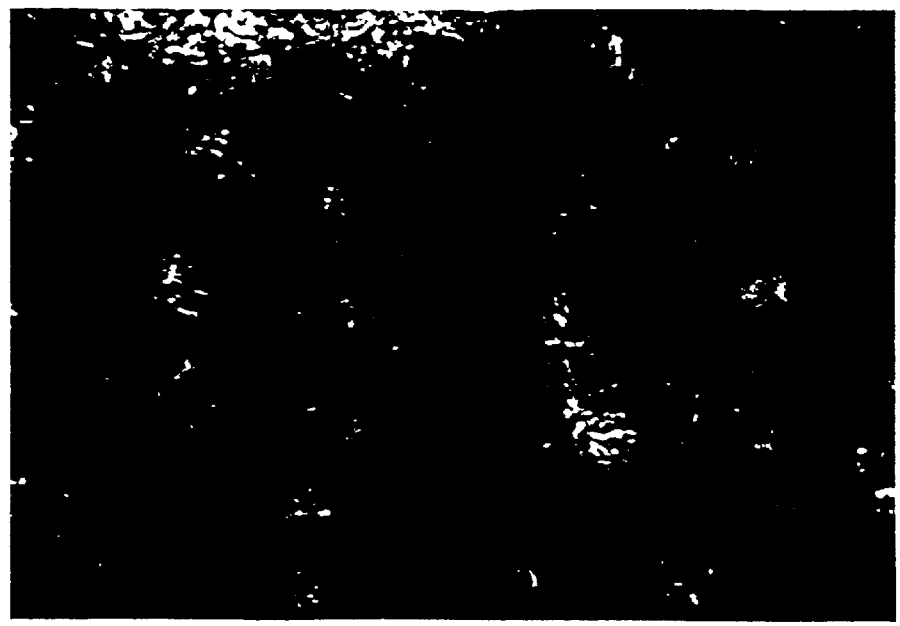
FIG. 6 is an environmental scanning electron micrograph of an etched surface of melt-irradiated UHMWPE showing its crystalline structure at approximately the same magnification as in FIG. 5.

FIG. 4 shows an ESEM (magnification of 10,000×) of an etched surface of conventional UHMWPE (GUR 415; unheated; unirradiated). FIG. 5 shows an ESEM (magnification of 10,500×) of an etched surface of melt-irradiated UHMWPE (GUR 415; melted; 20 MRad). The ESEMs indicated a reduction in size of the crystallites and the occurrence of imperfect crystallization in the melt-irradiated UHMWPE as compared to the conventional UHMWPE.

(G) Fourier Transform Infra Red Spectroscopy (FTIR)

FTIR of the samples was performed using a microsampler on the samples rinsed with hexane to remove surface impurities. The peaks observed around 1740 to 1700 $cm^{-1}$ are bands associated with oxygen containing groups. Hence, the ratio of the area under the carbonyl peak at 1740 $cm^{-1}$ to the area under the methylene peak at 1460 $cm^{-1}$ is a measure of the degree of oxidation.

The FTIR spectra indicate that the melt-irradiated UHMWPE sample showed more oxidation than the conventional unirradiated UHMWPE control, but a lot less oxidation than an UHMWPE sample irradiated in air at room temperature and given the same irradiation dose as the melt-irradiated sample.

(H) Electron Paramagnetic Resonance (EPR)

EPR was performed at room temperature on the samples which were placed in a nitrogen atmosphere in an air tight quartz tube. The instrument used was the Bruker ESP 300 EPR spectrometer and the tubes used were Taperlok EPR sample tubes obtained from Wilmad Glass Company, Buena, N.J.

The unirradiated samples do not have any free radicals in them since irradiation is the process which creates free radicals in the polymer. On irradiation, free radicals are created which can last for several years under the appropriate conditions.

The EPR results indicate that the melt-irradiated sample did not show any free radicals when studied using an EPR immediately after irradiation, whereas the sample which was irradiated at room temperature under nitrogen atmosphere showed trans-vinylene free radicals even after 266 days of storage at room temperature. The absence of free radicals in the melt-irradiated UHMWPE sample means that any further oxidative degradation was not possible.

(I) Wear

The wear resistance of the samples was measured using a bi-axial pin-on-disk wear tester. The wear test involved the rubbing action of UHMWPE pins (diameter=9 mm; height=13 mm) against a Co—Cr alloy disk. These tests were carried out to a total of 2 million cycles. The unirradiated pin displayed a wear rate of 8 mg/million-cycles while the irradiated pin had a wear rate of 0.5 mg/million cycles. The results indicate that the melt-irradiated UHMWPE has far superior wear resistance than the unirradiated control.

Example 3

Method of Making Melt-Irradiated UHMWPE Conventional Articular Cups

This example illustrates electron irradiation of a melted UHMWPE conventional articular cup.

A conventional articular cup (high conformity unsterilized UHMWPE cup made by Zimmer, Inc., Warsaw, Ind.) of internal diameter 26 mm and made of GUR 415 ram extruded bar stock, was irradiated under controlled atmosphere and temperature conditions in an air-tight chamber with a titanium cup holder at the base and a thin stainless steel foil (0.001 inches thick) at the top. The atmosphere within this chamber consisted of low oxygen nitrogen gas (<0.5 ppm oxygen gas) (obtained from AIRCO, Murray Hill, N.H.). The pressure in the chamber was approximately 1 atm. The chamber was heated using a 270 W heating mantle at the base of the chamber which was controlled using a temperature controller and a variac. The chamber was heated such that the temperature at the top surface of the cup rose at approximately 1.5° to 2° C./min, finally asymptotically reaching a steady state temperature of approximately 175° C. Due to the thickness of the sample cup and the particular design of the equipment used, the steady state temperature of the cup varied between 200° C. at the base to 175° C. at the top. The cup was held at these temperatures for a period of 30 minutes before starting the irradiation.

Irradiation was done using a van de Graaff generator with electrons of energy 2.5 MeV and a dose rate of 1.67 MRad/min. The beam entered the chamber through the thin foil at top and hit the concave surface of the cup. The dose received by the cup was such that a maximum dose of 20 MRad was received approximately 5 mm below the surface of the cup being hit by the electrons. After irradiation, the heating was stopped and the cup was allowed to cool to room temperature (approximately 25° C.) while still in the chamber with nitrogen gas. The rate of cooling was approximately 0.5° C./min. The sample was removed from the chamber after the chamber and the sample had reached room temperature.

The above irradiated cup which increases in volume (due to the decrease in density accompanying the reduction of crystallinity following melt-irradiation) can be remachined to the appropriate dimensions.

Example 4

Swell Ratio and Percent Extract at Different Depths for Melt-Irradiated UHMWPE Articular Cups This example illustrates the swell ratio and percent extract at different depths of the melt-irradiated articular cup obtained from Example 3. Samples of size 2 mm×2 mm×2 mm were cut from the cup at various depths along the axis of the cup. These samples were then kept submerged in Decalin at 150° C. for a period of 24 hours. An antioxidant (1% N-phenyl-2-naphthylamine) was added to the Decalin to prevent degradation of the sample. The swell ratio and percent extract were calculated by measuring the weight of the sample before the experiment, after swelling for 24 hours, and after vacuum drying the swollen sample. The results are shown in Table 6.

TABLE 6

The Swell Ratio and Percent Extract at Different Depths on the Melt-Irradiated UHMWPE Articular Cup

| Depth (mm) | Swell Ratio (Decalin, 150° C., 1 day) | % Extract |
|---|---|---|
| 0–2 | 2.43 | 0.0 |
| 2–4 | 2.52 | 0.0 |
| 4–6 | 2.51 | 0.0 |

TABLE 6-continued

The Swell Ratio and Percent Extract at Different Depths
on the Melt-Irradiated UHMWPE Articular Cup

| Depth (mm) | Swell Ratio (Decalin, 150° C., 1 day) | % Extract |
|---|---|---|
| 6–8 | 2.64 | 0.0 |
| 8–10 | 2.49 | 0.0 |
| 10–12 | 3.68 | 0.0 |
| >12 | 6.19 | 35.8 |
| Unirradiated | Dissolves | Approx. 100% |

The results indicate that the UHMWPE in the cup had been crosslinked to a depth of 12 mm due to the melt-irradiation process to such an extent that no polymer chains dissolved out in hot Decalin over 24 hours.

Example 5

Crystallinity and Melting Point at Different Depths for the Melt-Irradiated UHMWPE Articular Cups This example illustrates the crystallinity and melting point at different depths of the melt-irradiated cup obtained from Example 3.

Samples were taken from the cup at various depths along the axis of the cup. The crystallinity is the fraction of the polymer that is crystalline. The crystallinity was calculated by knowing the weight of the sample (w, in g), the heat absorbed by the sample in melting (E, in cal which was measured experimentally using a Differential Scanning Calorimeter at 10° C./min) and the heat of melting of polyethylene crystals ($\Delta H=69.2$ cal/g), using the following equation:

$$\% \ crystallinity = \frac{E}{w \cdot \Delta H}$$

Figure 7:
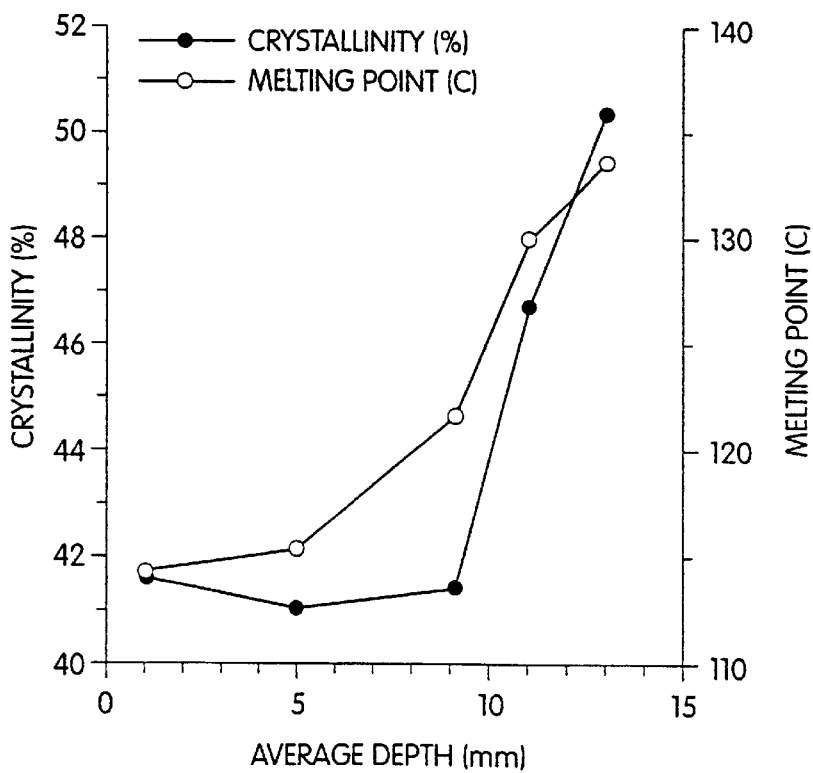
FIG. 7 is a graph showing the crystallinity and melting point at different depths of a melt-irradiated UHMWPE cup.

The melting point is the temperature corresponding to the peak in the DSC endotherm. The results are shown in FIG. 7.

The results indicate that the crystallinity and the melting point of the melt-irradiated UHMWPE in the articular cups obtained from Example 3 were much lower than the corresponding values of the conventional UHMWPE, even to a depth of 1 cm (the thickness of the cup being 1.2 cms).

Example 6

Second Method of Making Melt-Irradiated UHMWPE Articular Cups

This example illustrates a method for making articular cups with melt-irradiated UHMWPE.

Conventional UHMWPE bar stock made from GUR 415 (obtained from West Lake Plastics, Lenni, Pa.) was machined to the shape of a cylinder, of height 4 cm and diameter 5.2 cm. One circular face of the cylinder was machined to include an exact hemispherical hole, of diameter 2.6 cm, such that the axis of the hole and the cylinder coincided. This specimen was enclosed in an air-tight chamber with a thin stainless steel foil (0.001 inches thick) at the top. The cylindrical specimen was placed such that the hemispherical hole faced the foil. The chamber was then flushed and filled with an atmosphere of low oxygen nitrogen gas (<0.5 ppm oxygen gas) obtained from AIRCO, Murray Hill, N.J.). Following this flushing and filling, a slow continuous flow of nitrogen was maintained while keeping the pressure in the chamber at approximately 1 atm. The chamber was heated using a 270 W heating mantle at the base of the chamber which was controlled using a temperature controller and a variac. The chamber was heated such that the temperature at the top surface of the cylindrical specimen rose at approximately 1.5° C. to 2° C./min, finally asymptomatically reaching a steady state temperature of approximately 175° C. The specimen was then held at this temperature for a period of 30 minutes before starting irradiation.

Irradiation was done using a van de Graaff generator with electrons of energy 2.5 MeV and a dose rate of 1.67 MRad/min. The beam entered the chamber through the thin foil at top and hit the surface with the hemispherical hole. The dose received by the specimen was such that a maximum dose of 20 MRad was received approximately 5 mm below the surface of the polymer being hit by the electrons. After irradiation, the heating was stopped and the specimen was allowed to cool to room temperature (approximately 25° C.) while still in the chamber with nitrogen gas. The rate of cooling was approximately 0.5° C./min. The sample was removed from the chamber after the chamber and the sample had reached room temperature.

This cylindrical specimen was then machined into an articular cup with the dimensions of a high conformity UHMWPE articular cup of internal diameter 26 mm manufactured by Zimmer, Inc., Warsaw, Ind., such that the concave surface of the hemispherical hole was remachined into the articulating surface. This method allows for the possibility of relatively large changes in dimensions during melt irradiation.

Those skilled in the art will be able to ascertain using no more than routine experimentation, many equivalents of the specific embodiments of the invention described herein. These and all other equivalents are intended to be encompassed by the following claims.

What is claimed is:

1. A method for making highly entangled and crosslinked ultra high molecular weight polyethylene, comprising the steps of:

providing conventional ultra high molecular weight polyethylene;

surrounding said ultra high molecular weight polyethylene with an inert material that is substantially free of oxygen;

heating said ultra high molecular weight polyethylene above the melting temperature of said ultra high molecular weight polyethylene for a time sufficient to enable the formation of entangled polymer chains in said ultra high molecular weight polyethylene;

irradiating said heated ultra high molecular weight polyethylene so as to trap the polymer chains in the entangled state; and cooling said irradiated ultra high molecular weight polyethylene to about 25° C.

2. The method of claim 1 wherein said ultra high molecular weight polyethylene in said providing step is selected from the group consisting of a powder, a bar stock, a shaped bar stock, a coating and a fabricated article.

3. The method of claim 1 wherein said ultra high molecular weight polyethylene in said providing step is a cup shaped article for use in a prosthesis.

4. The method of claim 1 wherein said ultra high molecular weight polyethylene in said providing step is machined bar stock.

5. The method of claim 1 wherein said ultra high molecular weight polyethylene in said providing step has an initial average molecular weight of greater than about 2 million.

6. The method of claim 1 wherein said temperature in said heating step is about 145° C. to about 230° C.

7. The method of claim 1 wherein said temperature in said heating step is about 175° C. to about 200° C.

8. The method of claim 1 wherein said temperature in said heating step is maintained for about 5 minutes to about 3 hours.

9. The method of claim 1 wherein said irradiating step uses irradiation selected from the group consisting of gamma irradiation and electron irradiation.

10. The method of claim 1 wherein said irradiating step delivers a dose of greater than about 1 MRad to said heated ultra high molecular weight polyethylene.

11. The method of claim 1 wherein said cooling step is at a rate greater than about 0.5° C./min.

12. The method of claim 1 further comprising the step of machining said cooled ultra high molecular weight polyethylene.

* * * * *